(12) United States Patent
Wu et al.

(10) Patent No.: US 11,452,754 B2
(45) Date of Patent: Sep. 27, 2022

(54) PHARMACEUTICAL COMPOSITION AND USES THEREOF

(71) Applicants: Taipei Chang Gung Memorial Hospital, Taipei (TW); Chang Gung University, Taoyuan (TW)

(72) Inventors: Yi-Hong Wu, Taipei (TW); Yueh Hsiang Huang, Taipei (TW); Jong-Hwei Su Pang, Taoyuan (TW)

(73) Assignees: TAIPEI CHANG GUNG MEMORIAL HOSPITAL, Taipei (TW); CHANG GUNG UNIVERSITY, Taoyuan (TW)

( * ) Notice: Subject to any disclaimer, the term of this patent is extended or adjusted under 35 U.S.C. 154(b) by 20 days.

(21) Appl. No.: 16/785,880

(22) Filed: Feb. 10, 2020

(65) Prior Publication Data
US 2020/0268820 A1  Aug. 27, 2020

Related U.S. Application Data

(60) Provisional application No. 62/810,088, filed on Feb. 25, 2019.

(51) Int. Cl.
*A61K 36/71* (2006.01)
*A61K 36/25* (2006.01)
*A61K 36/076* (2006.01)
*A61P 3/06* (2006.01)
*A61P 3/10* (2006.01)
*A61P 3/04* (2006.01)
*A61K 36/894* (2006.01)

(52) U.S. Cl.
CPC ............ *A61K 36/71* (2013.01); *A61K 36/076* (2013.01); *A61K 36/25* (2013.01); *A61K 36/894* (2013.01); *A61P 3/04* (2018.01); *A61P 3/06* (2018.01); *A61P 3/10* (2018.01)

(58) Field of Classification Search
None
See application file for complete search history.

(56) References Cited

FOREIGN PATENT DOCUMENTS

| CN | 1259935 | C | * | 6/2006 |
| CN | 101554228 | A | * | 10/2009 |
| CN | 103157059 | A | * | 6/2013 |
| KR | 20140112772 | A | * | 9/2014 |

OTHER PUBLICATIONS

CN-1259935-C translated doc (Year: 2006).*
CN-101554228-A translated doc (Year: 2009).*
CN-103157059-A translated doc (Year: 2013).*
KR-20140112772-A translated doc (Year: 2014).*
Nasri (Metformin: Current knowledge, Journal of Research in Medical Sciences, Jul. 2014, 19:658-64). (Year: 2014).*
Jun Yin et al., "Efficacy of berberine in patients with type 2 diabetes mellitus," Metabolism Clinical and Experimental, May 2008, pp. 712-717, vol. 57.
Qi-Ming Chen et al., "Studies on the Hypoglycemic Effect of Coptis Chinensis and Berberine," Acta pharmaceutica Sinica, Jun. 1986, pp. 401-406, vol. 21(6) (English language abstract included).
Biao Chen et al., "Regulatory effect of coptisine on key genes involved in cholesterol metabolism," China Journal ol Chinese Materia Medica, Apr. 2015, pp. 1548-1553, vol. 40, No. 8 (English language abstract included).
Zhao Jin Xi, "Shenling Baizhu Wan and the prevention of diabetes and its complications," Diabetes New World, Apr. 2006.
Haixiong Lin et al., "Effects of Shenling Baizhu Powder on Blood Lipid, Glucose and Leptin in Hyperlipidemia Mice" Chinese Archives of Traditional Chinese Medicine, Jan. 2017, pp. 143-145, vol. 35, No. 1 (English language abstract included).
Office Action for related Taiwan application 109104049 filed Feb. 10, 2020, dated Jun. 17, 2021.

* cited by examiner

*Primary Examiner* — Terry A McKelvey
*Assistant Examiner* — Jacob A Boeckelman
(74) *Attorney, Agent, or Firm* — Piloff Passino & Cosenza LLP; Sean A. Passino; Rachel K. Pilloff

(57) ABSTRACT

Pharmaceutical compositions containing a combination of rhizoma coptidis and a herbal composition comprises at least one herb selected from the group consisting of Radix Ginseng, Poria, Rhizoma Atractylodis macrocephalae, Semen Lablab album, Rhizoma Dioscoreae, Embryo Nelumbinis, Radix Platycodonis, Semen Coicis, Fructus Amomi, Fructus Jujubae and Radix Glycyrrhizae are disclosed. Methods of treating diseases by administering an effective amount of the pharmaceutical composition are also provided.

15 Claims, 3 Drawing Sheets

PHARMACEUTICAL COMPOSITION AND USES THEREOF

CROSS-REFERENCE TO RELATED APPLICATION

This application claims priority to U.S. Application No. 62/810,088, filed on 25 Feb. 2019, the entire disclosure of which is incorporated herein by reference.

TECHNOLOGY FIELD

The present invention relates to pharmaceutical compositions and the use of the pharmaceutical compositions for the treating metabolic syndrome, obesity, diabetes and/or hyperlipidemia.

BACKGROUND OF THE INVENTION

Obesity is considered a risk factor for a number of disorders that can manifest at an early age, such as metabolic syndrome (ACB Rizzo et al., Nutr J. 2013; 12: 19). Type 2 diabetes frequently develops as the metabolic syndrome further deteriorates.

Diabetes is a chronic metabolic disease with increased prevalence worldwide. According to the International Diabetes Federation (IDF) guidelines, achieving $HbA_{1c}$ below 7.0% (53 mmol/mol) minimizes the risk of developing diabetes-related complications, such as cardiovascular disease, nephropathy, neuropathy and retinopathy. Previous studies have shown that less than one-third of type 2 diabetes patients taking oral anti-diabetic medications had achieved the goal of $HbA_{1c}<7.0\%$ (53 mmol/mol) in China and this unsatisfactory glycemic control is also noted in other countries. Many diabetic patients taking three or more oral hypoglycemic agents (OHAs) still cannot effectively lower their $HbA_{1c}$ levels, a condition sometimes referred to as treatment-resistant type 2 diabetes (, see AJ Sheen, Pharmacotherapy of 'treatment resistant' type 2 diabetes, Expert Opinion on pharmacotherapy, 18(5), 2017, 503-515). The failure of oral hypoglycemic therapy to control $HbA_{1c}$ levels implies resorting to injectable insulin, even though hypoglycemia and weight gain are common side effects.

There is still a need for a more effective and safe treatment for obesity, metabolic syndrome, diabetes (such as treatment-resistant type 2 diabetes) and related complications. The present invention addresses this need and other needs.

BRIEF SUMMARY OF THE INVENTION

In one embodiment, the present invention discloses pharmaceutical compositions comprising (a) about 30% to about 90% by weight of Rhizoma Coptidis; and (b) about 10% to about 70% by weight of a herbal composition, said herbal composition comprises at least one herb selected from the group consisting of Radix Ginseng, Poria, Rhizoma Atractylodis macrocephalae, Semen Lablab album, Rhizoma Dioscoreae, Embryo Nelumbinis, Radix Platycodonis, Semen Coicis, Fructus Amomi, Fructus Jujubae and Radix Glycyrrhizae.

In yet another embodiment, the pharmaceutical compositions are effective in treating one or more of the following diseases: metabolic syndrome, obesity, diabetes or hyperlipidemia, by administering an effective amount of the pharmaceutical composition described herein to a subject in need thereof, wherein administration of the pharmaceutical composition results in a decrease in the subject's plasma lipids, plasma sugar, body weight blood pressure, or a combination thereof to a physiological level. In one embodiment, the method for treating diabetes further comprises administering an effective amount of a hypoglycemic agent. In one embodiment, the method for treating hyperlipidemia further comprises administering an effective amount of a cholesterol reducing agent.

Also provided are the uses of the pharmaceutical compositions described herein for the manufacture of a medicament for treating metabolic syndrome, diabetes, hyperlipidemia and/or obesity in a subject.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

DETAILED DESCRIPTION

Definitions

Figure 1:
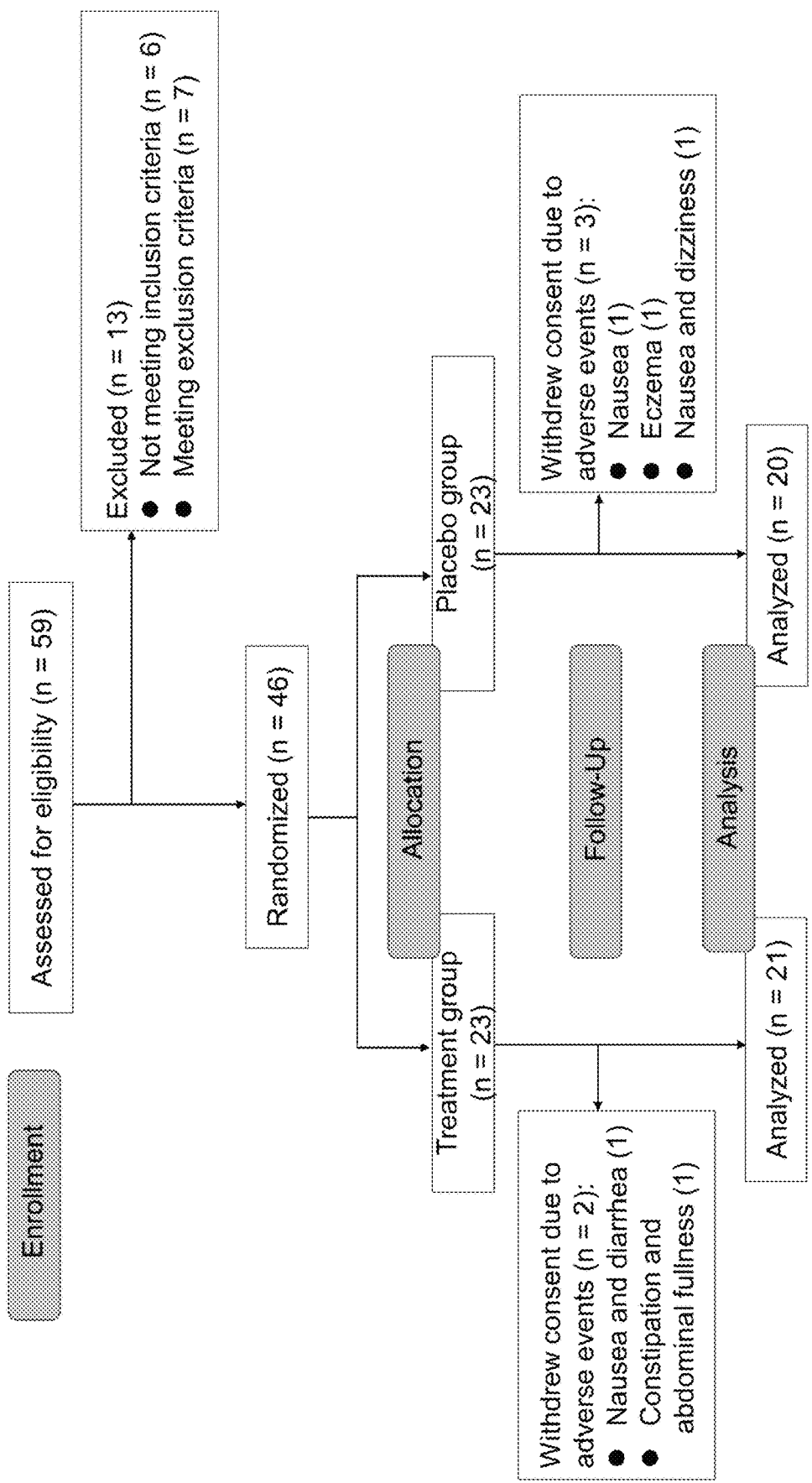
FIG. 1 is a flow diagram illustrates schematically the enrollment, randomization, and treatment of the clinical trial of Example 1.

As employed above and throughout the disclosure, the following terms, unless otherwise indicated, shall be understood to have the following meanings.

As used herein, the singular forms "a," "an," and "the" include the plural reference unless the context clearly indicates otherwise.

An "effective amount," as used herein, includes a dose of the pharmaceutical composition that is sufficient to treat or ameliorate at least one symptom of diabetes, obesity, metabolic syndrome or hyperlipidemia.

The term "treating," "treated," or "treatment" as used herein refers to palliative uses or results, and/or slowing or inhibiting the advancement of diabetes, obesity, metabolic syndrome or hyperlipidemia.

The term "diabetes" as used herein includes but not limited to pre-diabetes, type 1 diabetes, type 2 diabetes, gestational diabetes, beta cell genetic deficiency, insulin resistance, treatment-resistant diabetes or at least one diabetic complication. In an embodiment, a subject has treatment-resistant diabetes if the subject has type 2 diabetes and been treated with ≥3 classes of OHAs with $HbA_{1c}>7.0\%$.

As used herein, the term "obesity" is meant to include any fat or weight in a subject who desires to lose such weight or fat. Thus, reference to the "treatment or prevention of obesity" encompasses any subject who desires to reduce their body weight or reduce adipose (fat) tissue mass, regardless of their body weight or adipose tissue mass.

The term "hyperlipidemia" as used herein refers to a pathological condition manifest by elevated serum concentrations of total cholesterol, LDL cholesterol, or triglycerides, or at least one hyperlipidemia complications, such as atherosclerosis or cardiovascular disease (CVD). The cholesterol level may be above an accepted normal threshold level, such as those promulgated by the National Heart Lung and Blood Institute (NHLBI). The accepted normal threshold cholesterol level may vary from subject to subject based on various risk factors, such as for example a prior history of CVD.

Metabolic syndrome is a group of risk factors characterized by impaired glucose tolerance, reduced insulin sensitivity, hyperlipidemia and excess body fat around waist.

The term "subject" as used herein typically refers to a human or an animal has or suspected of having diabetes, obesity, hyperlipidemia or metabolic syndrome Subjects without known or suspected diabetes, obesity, hyperlipidemia or metabolic syndrome, such as research subjects, are also included within the scope of the term "subject."

All numbers herein may be understood as modified by "about." As used herein, the term "about" is meant to encompass variations of ±10%.

Pharmaceutical Composition

The present invention provides a pharmaceutical composition, comprising a combination of (a) about 30% to about 90% by weight of Rhizoma Coptidis; and (b) about 10% to about 70% by weight of a herbal composition, wherein said herbal composition comprises at least one, two, three, four, five, six, seven, eight, nine, ten or all of the herbs selected from the group consisting of Radix Ginseng, Poria, Rhizoma Atractylodis macrocephalae, Semen Lablab album, Rhizoma Dioscoreae, Embryo Nelumbinis, Radix Platycodonis, Semen Coicis, Fructus Amomi, Fructus Jujubae and Radix Glycyrrhizae, preferably by advantageous synergistic effects of the combinations.

In one exemplary embodiment, the pharmaceutical composition includes about 30, 35, 40, 45, 50, 55, 60, 65, 70, 75, 80, 85, 90% or any range of % therein between (e.g., 30-90%, 35-80%, 40-70%, 45-60%) by weight of Rhizoma Coptidis. Each gram of Rhizoma Coptidis in the pharmaceutical composition includes about 10 to 100 mg, 20 to 80 mg or 30 to 50 mg of berberine. In one exemplary embodiment, the pharmaceutical composition includes about 10, 15, 20, 25, 30, 35, 40, 45, 50, 55, 60, 65, 70% or any range of % therein between (e.g., 10-70%, 20-65%, 30-60%) by weight of a herbal composition.

In certain embodiments, the herbal composition for use in the present invention comprises Radix Ginseng, Poria, Rhizoma Atractylodis macrocephalae, Semen Lablab album, Rhizoma Dioscoreae, Embryo Nelumbinis, Radix Platycodonis, Semen Coicis, Fructus Amomi, Fructus Jujubae and Radix Glycyrrhizae. In an exemplary embodiment, the herbal composition comprises about 11-13% by weight of Radix Ginseng, about 11-13% by weight of Poria, about 11-13% by weight of Rhizoma Atractylodis macrocephalae, about 8-10% by weight of Semen Lablab album, about 11-13% by weight of Rhizoma Dioscoreae, about 5-7% by weight of Embryo Nelumbinis, about 5-7% by weight of Radix Platycodonis, about 5-7% by weight of Semen Coicis, about 5-7% by weight of Fructus Amomi, about 5-7% by weight of Fructus Jujubae and about 11-13% by weight of Radix Glycyrrhizae.

In certain embodiments, the herbal composition comprises Radix Ginseng, Poria, Rhizoma Atractylodis macrocephalae, Semen Lablab album, and Rhizoma Dioscoreae. In an exemplary embodiment, the herbal composition comprises about 10 to 20% by weight of Radix Ginseng, about 10 to 20% by weight of Poria, about 10 to 20% by weight of Rhizoma Atractylodis macrocephalae, about 8 to 18% by weight of Semen Lablab album, and about 10 to 20% by weight of Rhizoma Dioscoreae.

The herbs in the herbal composition and Rhizoma Coptidis can be raw herb, grinded powder, decoction, crude extract or extracted granule of the raw herb. In an exemplary embodiment, the extracted granule is prepared by aqueous extraction wherein the raw herb (can be optionally grinded before extraction to achieve the best extraction outcome) is heated in water or solvent, followed by filtration, concentration (wherein the liquid extract is condensed by vacuum or low pressure concentration) and drying. In another exemplary embodiment, the extracted granules are prepared by fluid-bed granulation process.

Rhizoma Coptidis contains berberine, which cause poor drug compliance due to its bitter taste and side effects such as gastrointestinal upset. The poor drug compliance and side effects maybe overcome by administering a lower dosage of Rhizoma Coptidis, in combination with the herbal composition of the present invention, to achieve the desired therapeutic effect. The observed synergistic effect of a pharmaceutical composition comprising a combination of Rhizoma Coptidis and the herbal composition of the present invention may afford effective treatment of diabetes, metabolic syndrome, hyperlipidemia or obesity wherein the lower dosage of Rhizoma Coptidis or the herbal composition would not be sufficient to have a therapeutic effect when used in monotherapy.

The pharmaceutical compositions to be administered according to the methods provided herein can be readily formulated with, prepared with, or administered with, a pharmaceutically acceptable carrier. Such preparations may be prepared by various techniques, including bringing into association active components of the pharmaceutical compositions and an appropriate carrier (e.g., a liquid carriers, a solid carriers, or both).

The pharmaceutical compositions provided herein may optionally include anti-oxidants, buffers, bacteriostatic agents, suspending agents thickening agents, preservatives, co-solvents and viscosity building agents or other therapeutic ingredients. The carrier and other therapeutic ingredients must be acceptable in the sense of being compatible with the pharmaceutical composition and not deleterious to the subject.

The pharmaceutical compositions are administered in an amount effective to reduce the symptom or signs of diabetes, metabolic syndrome, obesity or hyperlipidemia, or to induce a therapeutic response in a subject, including a human with diabetes, metabolic syndrome, obesity or hyperlipidemia. The dosage of the pharmaceutical composition administered will depend on the severity of the condition being treated, the particular formulation, and other clinical factors such as weight and the general condition of the subject and route of administration. Useful dosages of the pharmaceutical compositions provided herein are determined by comparing their in vitro activity, and in vivo activity in animal models. Methods for the extrapolation of effective dosages in mice, and other animals, to humans are known in the art; for example, see U.S. Pat. No. 4,938,949, which is incorporated by reference herein.

In accordance with the methods provided herein, the pharmaceutical composition is delivered by any of a variety of routes including, but not limited to, injection (e.g., subcutaneous, intramuscular, intravenous, intra-arterial, intraperitoneal, intradermal, intravitreal); cutaneously; dermally; transdermal; oral (e.g., tablet, powder, pill, lozenge, capsule, liquid, edible film strip, or any dose form which is suitable for herbal medicine); implanted osmotic pumps; suppository, aerosol spray, topical, ocular, nasal inhalation, pulmonary inhalation or impression into skin. In one embodiment, the pharmaceutical composition of the present invention can be administered orally as extracted granules.

The pharmaceutical composition may be administered in a single dose treatment or in multiple dose treatments, over a period of time appropriate to the condition being treated. The pharmaceutical composition may conveniently be administered at appropriate intervals, for example, once a day, twice a day, three times a day, four times a day, six times a day, once every second day, once every three days or until the symptoms and signs of the condition are resolved.

Methods for Treating Diabetes

The present invention provides a method for treating diabetes or its complications, comprising administering a therapeutically effective amount of the pharmaceutical composition described herein to a subject in need thereof. The administration of the pharmaceutical composition results in a decrease in the subject's plasma sugar, HbA1c, increase in the subject's plasma insulin or a combination thereof to a physiological level.

In one exemplary embodiment, the pharmaceutical composition administered corresponds to a daily dose of less than 1500 mg of berberine, such as 50 to 1000 mg, 75 to 750 mg, or 100 to 600 mg of berberine. In another exemplary embodiment the dose of berberine in each one of the pharmaceutical composition is about 50 to 400 mg, 50 to 300 mg, 50 to 200 mg or 50 to 150 mg.

In an exemplary embodiment, the method further comprises administering a hypoglycemic agent. Non limiting examples of hypoglycemic agent include insulin or an oral hypoglycemic agent such as biguanide (e.g., metformin, pheformin, and buformin); thiazolidinediones (e.g., rosiglitazone, pioglitazone, and troglitazone); sulfonylurea (e.g., glimepiride, glyburide, glipizide, chloropropamide, and tolbutamide), meglitinides (e.g., repaglinide, nateglinide); α-glucosidase inhibitors (e.g., miglitol, acarbose, and voglibose); SGLT2 inhibitor (e.g., Dapagliflozin, Empagliflozin, and Canagliflozin,); DPP-4 inhibitors (e.g., sitagliptin, vildagliptin and saxagliptin). The pharmaceutical composition and the hypoglycemic agent maybe administered concomitantly or non-concomitantly.

Methods for Treating Obesity

Accordingly, the present invention encompasses the treatment or prevention of obesity or its complications by administering a therapeutically effective amount of the pharmaceutical composition described herein to a subject in need thereof. The administration of the pharmaceutical composition causes the loss of weight, body fat, and/or the reduction of body mass index in a subject. The present invention encompasses a subject who simply desires to lose weight and is not necessarily suffering from obesity or being overweight or suffering from a weight-related disorder.

In one exemplary embodiment, the pharmaceutical composition administered corresponds to daily dose of 50 to 1000 mg, 75 to 750 mg, or 100 to 600 mg of berberine.

Methods for Treating Metabolic Syndrome

Methods of ameliorating one or more symptoms or disorders associated with metabolic syndrome are provided. The method typically involves administering a therapeutically effective amount of the pharmaceutical composition described herein to a subject in need thereof.

In certain embodiments, at least one the following symptoms or disorders is ameliorated after the administration of the pharmaceutical composition: insulin resistance, glucose intolerance, fatty liver disease, macrophage infiltrates into adipose tissue or obesity.

In one exemplary embodiment, the pharmaceutical composition administered corresponds to daily dose of 50 to 1000 mg, 75 to 750 mg, or 100 to 600 mg of berberine.

Methods for Treating Hyperlipidemia

Another embodiment of the invention provides a method for treating hyperlipidemia and/or preventing its complications in a patient in need thereof, comprising administering to the patient an effective amount of the pharmaceutical composition described herein to a subject in need thereof.

The method further comprises the administration of at least one additional cholesterol reducing agent. Such agents reduce serum cholesterol by partially or completely blocking de novo cholesterol synthesis. Cholesterol reducing agents encompass several classes of drugs that include HMG CoA reductase inhibitors (statins), γ-tocotrienol, bisphosphonates, cholesterol-ester-transfer-protein ("CETP") inhibitors, squalene synthase inhibitors, soluble guanylate cyclase modulators ("sGC modulators"), nicotinic acid and derivatives thereof (e.g. AGI-1067), or bile acid sequestrants.

The pharmaceutical composition and the cholesterol reducing agent maybe administered concomitantly or non-concomitantly.

The methods described herein also encompass research methods and uses, including in vitro and in vivo methods of treating or inhibiting the progression of diabetes, obesity, metabolic syndrome or hyperlipidemia in the subject.

Embodiments of the present invention are illustrated by the following examples, which are not to be construed in any way as imposing limitations upon the scope thereof. During the studies described in the following examples, conventional procedures were followed, unless otherwise stated. Some of the procedures are described below for illustrative purpose.

EXAMPLES

Example 1

Clinical Trial on the Effect of the Pharmaceutical Composition

A randomized, double-blind, placebo-controlled trial was conducted to evaluate the effect of the pharmaceutical composition of the present invention on glycemic control, body weight, and plasma lipid levels.

The inclusion criteria for the clinical trial are: 1) diagnosed with type 2 diabetes and treated with ≥3 classes of OHAs with >6 months of poor glycemic controlled, defined as $HbA_{1c}$>7.0% or 53 mmol/mol; 2) 20-75 years of age; 3) BMI ≥23 kg/m².

The exclusion criteria are: 1) type 1, gestational, or other specific types of diabetes; 2) received insulin therapy in the past three months; 3) serious gastrointestinal (GI) tract diseases or illnesses, such as peptic ulcers or GI tract bleeding, diabetic ketoacidosis, nonketotic hyperosmolar diabetic coma, severe infection, or surgery in the previous month; 5) hepatic insufficiency with alanine aminotransferase (ALT) two times the upper limit of normal or renal insufficiency with estimated glomerular filtration rate (eGFR) <60; 6) uncontrolled hypertension (blood pressure ≥160/100 mmHg); 7) mental illness, addition to alcohol, psychoactive substances or other drugs; 8) pregnancy, lactation, or planning to become pregnant; 9) hemoglobin disease or chronic anemia; 10) any underlying conditions that could lead to poor compliance; 11) history of cerebrovascular disease or myocardial infarction; 12) received Chinese herbal medicine treatment in the past two weeks.

As illustrated in FIG. 1, a total of 46 subjects were enrolled, 23 subjects were randomized into the treatment group and the placebo group respectively. There was no statistically significant difference in age, body weight, BMI, blood pressures, HbA$_{1c}$, 2 hPG, lipid levels between the subjects in the treatment group and the placebo group at baseline.

Subjects in the treatment group received two treatment packs three times daily with warm water after a meal. Each treatment pack comprises 3 g of the pharmaceutical composition of the present invention, which includes 50% by weight of Rhizoma Coptidis extracted granules of and 50% by weight of the extracted granules of the herbal composition described herein. The weight ratios of herbs in the herbal composition are: Radix Ginseng: Poria: Rhizoma Atractylodis macrocephalae: Semen Lablab album: Rhizoma Dioscoreae: Embryo Nelumbinis: Radix Platycodonis: Semen Coicis: Fructus Amomi: Fructus Jujubae: Radix Glycyrrhizae=3:3:3:2.3:3:1.5:1.5:1.5:1.5:3. Each gram of the pharmaceutical composition contained 20.05 mg of berberine.

Subjects in the placebo group received two placebo packs comprises 3 g of placebo granules, which are identical to the treatment packs in appearance. All of the subjects continued to receive their oral hypoglycemic agents (OHAs) without any change in dose or medication.

During the 12-week study period, subjects were assessed on regular intervals for the outcome variables listed in Table 1, drug compliance and side effects.

TABLE 1

The effect of 12-week treatment of the pharmaceutical composition of the present invention on body weight, glycemic control and lipid profiles.

|  | YH1 Group (n = 21) | Placebo Group (n = 20) | Wilcoxon rank-sum test p-Value |
|---|---|---|---|
| Weight (kg) | | | |
| Median at 12 week (Min, Max) | 73.6 (57.7, 108.2) | 74.3 (60.9, 87.6) | |
| Relative Change (%) | −0.5 (−3.2, 1.7) | 0.6 (−1.7, 4.2) | 0.030* |
| Waist circumference (cm) | | | |
| Median at 12 week (Min, Max) | 90.5 (79.0, 112.5) | 93.3 (81.5, 105.5) | |
| Relative Change (%) | −1.1 (−4.1, 2.2) | 0.5 (−2.8, 3.2) | 0.012* |
| HbA1c (%) | | | |
| Median at 12 week (Min, Max) | 7.6 (6.0, 9.3) | 8.7 (7.8, 10.2) | |
| Relative Change (%) | −11.1 (−30.2, 14.1) | 0.0 (−20.4, 7.3) | 0.008** |
| FPG (mg/dL) | | | |
| Median at 12 week (Min, Max) | 136.0 (83.0, 223.0) | 167.5 (112.0, 261.0) | |
| Relative Change (%) | −12.0 (−54.1, 51.7) | 5.0 (−27.3, 72.4) | 0.066 |
| 2hPG (mg/dL) | | | |
| Median at 12 week (Min, Max) | 172.0 (75.0, 286.0) | 253.0 (152.0, 355.0) | |
| Relative Change (%) | −26.2 (−60.3, 94.1) | 5.1 (−43.0, 90.6) | 0.006** |
| HOMA-β | | | |
| Median at 12 week (Min, Max) | 45.4 (13.7, 230.4) | 20.2 (9.2, 72.0) | |
| Relative Change (%) | 68.9 (−59.5, 399.2) | −1.4 (−63.2, 116.7) | 0.001** |
| Total cholesterol (mg/dL) | | | |
| Median at 12 week (Min, Max) | 152.0 (90.0, 213.0) | 172.0 (105.0, 238.0) | |
| Relative Change (%) | −21.6 (−38.9, 8.1) | −5.6 (−27.8, 58.2) | 0.004** |
| HDL-C (mg/dL) | | | |
| Median at 12 week (Min, Max) | 41.0 (27.0, 59.0) | 43.0 (30.0, 56.0) | |
| Relative Change (%) | −9.3 (−26.2, 13.9) | −3.1 (−18.6, 20.5) | 0.059 |
| LDL-C (mg/dL) | | | |
| Median at 12 week (Min, Max) | 86.0 (44.0, 152.0) | 107.5 (44.0, 170.0) | |
| Relative Change (%) | −17.4 (−54.1, 48.3) | −5.7 (−27.9, 83.6) | 0.023* |
| Triglycerides (mg/dL) | | | |
| Median at 12 week (Min, Max) | 109.0 (44.0, 347.0) | 180.0 (49.0, 286.0) | |
| Relative Change (%) | −29.5 (−60.7, 32.0) | 5.2 (−67.8, 59.5) | 0.004** |
| Triglycerides/HDL-C | | | |
| Median at 12 week (Min, Max) | 2.4 (1.3, 10.2) | 4.5 (1.0, 9.5) | |
| Relative Change (%) | −25.8 (−62.3, 27.5) | 0.2 (−64.9, 85.9) | 0.051 |

*p < .05;
**p < .01

FPG = fasting plasma glucose; 2hPG = 2-hour postprandial plasma glucose; HOMA-β = homeostatic model assessment of β cell function; ALT = alanine aminotransferase; HDL-C = high-density lipoprotein cholesterol; LDL-C = low-density lipoprotein cholesterol.

There was a significant reduction in the body weight, waist circumference, HbA$_{1c}$, 2 h PG, triglyceride, total cholesterol, and LDL-C and a significant increase in HOMA-$\beta$ after 12-weeks of treatment with the pharmaceutical composition of the present invention.

Figure 2A:
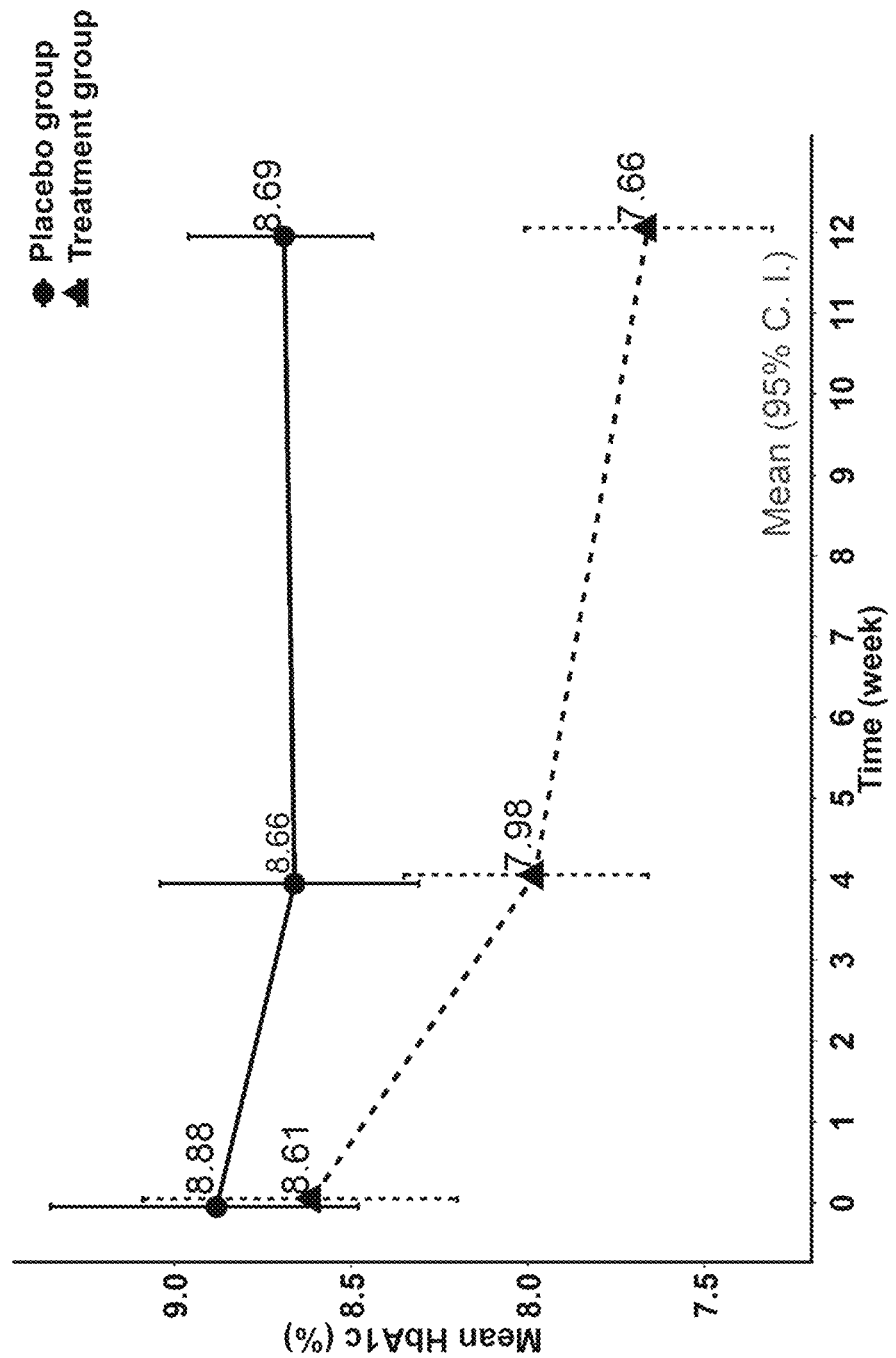
FIG. 2A and FIG. 2B are line graphs illustrating the percentage change in $HbA_{1c}$ and mean 2-hour postprandial plasma glucose (2 hPG) level of the placebo group and the treatment group.
Figure 2B:
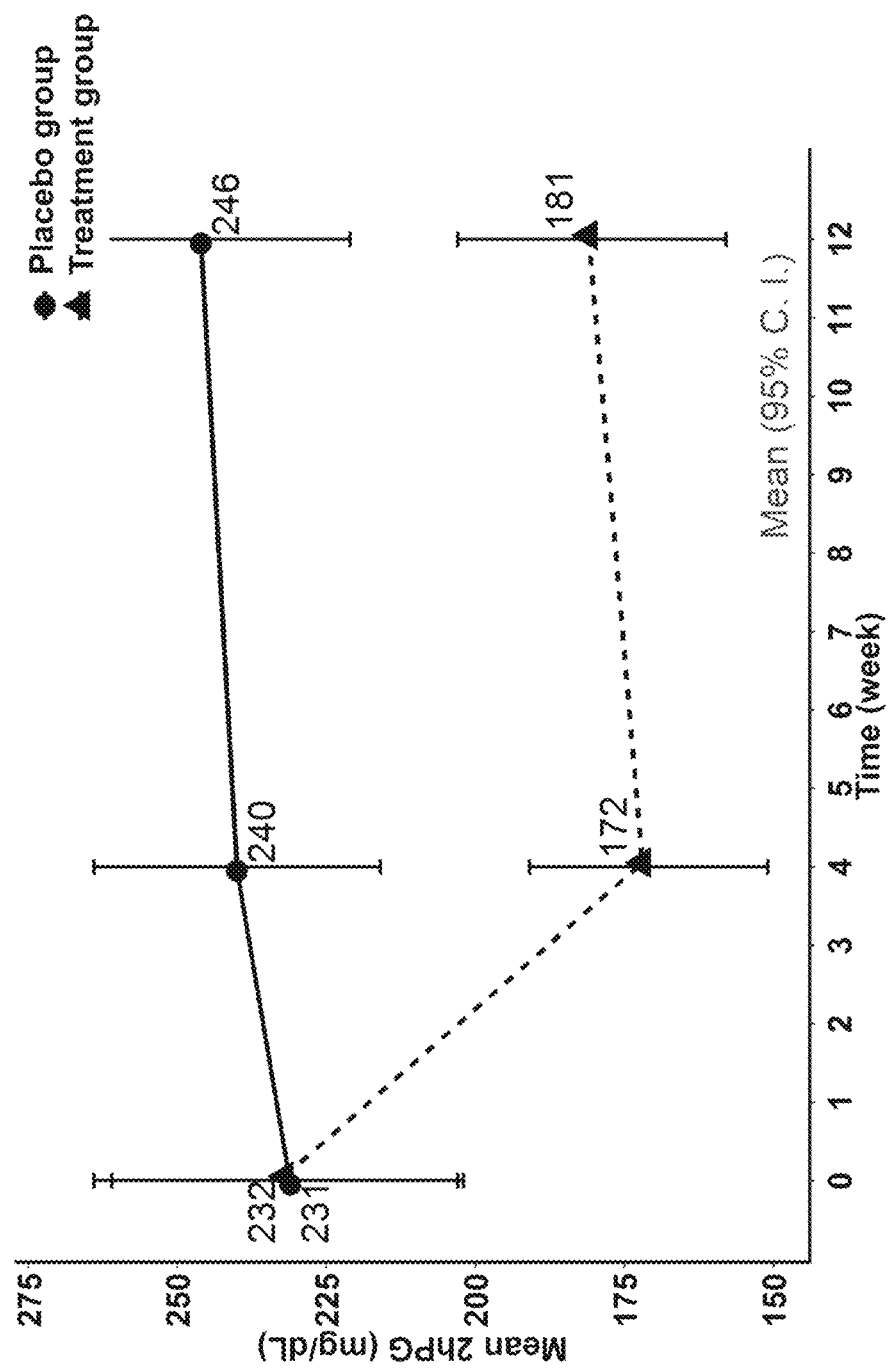

FIG. 2A shows a significant reduction in HbA$_{1c}$ and FIG. 2B shows a significant reduction of 2 hPG in the treatment group compared to the placebo group over the 12-week study period.

No serious adverse events were reported in the treatment group or placebo group. Liver and kidney functions were monitored during the 12-week study without significant changes. Incidences of diarrhea in the treatment and placebo groups were 30.4% and 13.0%, respectively, but subjects tolerated well without any decrease of dosage. Other gastrointestinal adverse events, including nausea, bloating, or gastroesophageal reflux disease, were 21.7% in the treatment group and 34.8% in placebo group.

The invention claimed is:

1. A pharmaceutical composition, comprising:
   (a) about 30% to about 90% by weight of Rhizoma Coptidis; and
   (b) about 10% to about 70% by weight of a herbal composition, said herbal composition comprises about 11-13% by weight of Radix Ginseng, about 11-13% by weight of Poria, about 11-13% by weight of Rhizoma Atractylodis macrocephalae, about 8-10% by weight of Semen Lablab album, about 11-13% by weight of Rhizoma Dioscoreae, about 5-7% by weight of Embryo Nelumbinis, about 5-7% by weight of Radix Platycodonis, about 5-7% by weight of Semen Coicis, about 5-7% by weight of Fructus Amomi, about 5-7% by weight of Fructus Jujubae and about 11-13% by weight of Radix Glycyrrhizae.

2. The pharmaceutical composition of claim 1, wherein said composition comprises about 40% to 80% by weight of Rhizoma Copitidis and about 20% to about 60% by weight of the herbal composition.

3. The pharmaceutical composition of claim 1, wherein the pharmaceutical composition is substantially free of mangiferin.

4. The pharmaceutical composition of claim 1, further comprising a hypoglycemic agent.

5. The pharmaceutical composition of claim 1, further comprising a cholesterol reducing agent.

6. A method for treating metabolic syndrome, obesity, diabetes or hyperlipidemia in a subject, comprising the step of administering the pharmaceutical composition of claim 1.

7. The method of claim 6, wherein said composition comprises about 40% to 80% by weight of Rhizoma Copitidis and about 20% to about 60% by weight of the herbal composition.

8. The method of claim 6, further comprising administering a hypoglycemic agent.

9. The method of claim 8, further comprising administering a cholesterol reducing agent.

10. The pharmaceutical composition of claim 1, said pharmaceutical composition increases HOMA-$\beta$ and reduces plasma sugar level of a treatment resistant type 2 diabetic patient taking the pharmaceutical composition compared to a treatment resistant type 2 diabetic patient not taking the pharmaceutical composition.

11. The pharmaceutical composition of claim 4, wherein the hypoglycemic agent is insulin, biguanide, thiazolidinediones, sulfonylurea, meglitinides, $\alpha$-glucosidase inhibitors, SGLT2 inhibitor, DPP-4 inhibitors or any combination thereof.

12. The method of claim 8, wherein the hypoglycemic agent is insulin, biguanide, thiazolidinediones, sulfonylurea, meglitinides, $\alpha$-glucosidase inhibitors, SGLT2 inhibitor, DPP-4 inhibitors or any combination thereof.

13. The method of claim 6, wherein said herbal composition comprises 11-13% by weight of Radix Ginseng, 11-13% by weight of Poria, 11-13% by weight of Rhizoma Atractylodis macrocephalae, 8-10% by weight of Semen Lablab album, 11-13% by weight of Rhizoma Dioscoreae, 5-7% by weight of Embryo Nelumbinis, 5-7% by weight of Radix Platycodonis, 5-7% by weight of Semen Coicis, 5-7% by weight of Fructus Amomi, 5-7% by weight of Fructus Jujubae and 11-13% by weight of Radix Glycyrrhizae.

14. The pharmaceutical composition of claim 1, wherein said herbal composition comprises 11-13% by weight of Radix Ginseng, 11-13% by weight of Poria, 11-13% by weight of Rhizoma Atractylodis macrocephalae, 8-10% by weight of Semen Lablab album, 11-13% by weight of Rhizoma Dioscoreae, 5-7% by weight of Embryo Nelumbinis, 5-7% by weight of Radix Platycodonis, 5-7% by weight of Semen Coicis, 5-7% by weight of Fructus Amomi, 5-7% by weight of Fructus Jujubae and 11-13% by weight of Radix Glycyrrhizae.

15. The pharmaceutical composition of claim 2, wherein said composition comprises 40% to 80% by weight of Rhizoma Copitidis and 20% to 60% by weight of the herbal composition.

* * * * *